US006251954B1

(12) United States Patent
Roulier et al.

(10) Patent No.: US 6,251,954 B1
(45) Date of Patent: Jun. 26, 2001

(54) AERATED COMPOSITION, PROCESS FOR ITS MANUFACTURE AND ITS USE

(75) Inventors: Veronique Roulier, Paris; Therese Daubige, Mousseaux les Bray, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/553,412

(22) Filed: Apr. 20, 2000

(30) Foreign Application Priority Data

Apr. 20, 1999 (FR) .................................................. 99 04968

(51) Int. Cl.⁷ ............................ A61K 47/32; A61K 7/00; A61K 9/14
(52) U.S. Cl. ...................... 514/772.4; 424/401; 424/486; 424/488
(58) Field of Search ...................................... 424/448, 449, 424/486, 488, 401; 427/208.4; 514/772.4, 772.3

(56) References Cited

U.S. PATENT DOCUMENTS 4,997,656 * 3/1991 Shikinami et al. .................. 424/448
5,674,561 * 10/1997 Dietz et al. ....................... 427/208.4

* cited by examiner

*Primary Examiner*—Thurman K. Page
*Assistant Examiner*—Blessing Fubara
(74) *Attorney, Agent, or Firm*—Oblon, Spivak, McClelland, Maier & Neustadt, P.C.

(57) ABSTRACT

An aerated composition comprising, in a physiologically acceptable medium, an oily phase dispersed in an aqueous phase, characterized in that it contains air or inert gas in a sufficient amount to have a relative density ranging from 0.2 to 0.8 and in that it comprises at least one amphiphilic polymer and at least one anionic surfactant. The composition exhibits a very fine texture and good cosmetic properties, while remaining very stable over time. In particular, it can constitute a cosmetic composition intended especially for treating and/or cleansing the skin, including the scalp, nails and/or hair and for making up the skin.

17 Claims, No Drawings

AERATED COMPOSITION, PROCESS FOR ITS MANUFACTURE AND ITS USE

BACKGROUND OF THE INVENTION

1. Field of the Invention

The present invention relates to an aerated composition comprising an associative polymer and an anionic surfactant and to its use in particular for treating and/or cleansing human skin, including the scalp, nails and/or hair, in particular for caring for dry skin and/or dry lips, and for making up the skin.

2. Description of the Related Art

Users of skin care products are increasingly looking for products which are pleasant to use and which have a novel texture. Until now, cosmetic compositions have been generally provided in the form of solutions, gels or more or less fluid creams.

Creams are conventionally composed of an emulsion. Emulsions comprise an aqueous phase and an oily phase dispersed in one another. Oil-in-water (O/W) emulsions, the external phase of which is the aqueous phase, are more particularly desired because they contribute more freshness on application than water-in-oil (W/O) emulsions comprising an oily external phase. Their feel and their application seem to be less greasy than those of a W/O emulsion. In addition, they make possible a high level of moisturizing, which is particularly useful in caring for dry skin or lips.

In order to confer a novel texture on emulsions, attempts have been made to introduce a gas, generally air, therein in order to confer on them a light texture and to give them the appearance of a foam. This is what is known as expansion. The aerated emulsions obtained are appreciated for their lightness on application. Nevertheless, they exhibit the disadvantage of being relatively unstable because of their low relative density and thus of separating out after a certain storage time. The application CH-A-674,804 discloses stabilization of an aerated cosmetic cream comprising an inert gas or air by the addition of an aqueous solution of a protein of animal origin. However, the use of such proteins is avoided in cosmetics.

Furthermore, the application JP-A-56/079613 discloses stable aerated surfactant-free compositions comprising from 5 to 20% of waxes, preferably waxes with a high melting point. The emulsions obtained are then stable but exhibit cosmetic properties which are unacceptable to the user. This is because these compositions comprise very little water and therefore lack freshness when applied to the skin. In addition, they comprise a significant amount of humectants, such as glycerol, which leads to a feeling of stickiness to the touch. In addition, the use of a wax with a high melting point in an amount of 5% results in heavy textures which are very difficult to apply to the skin.

The need thus remains for an emulsion which has the appearance of a foam, while comprising a large amount of water, and which is fresh and not sticky when applied to the skin.

SUMMARY OF THE INVENTION

The Inventors have found, unexpectedly, that the use of associative polymers in combination with an anionic surfactant makes it possible to obtain an aerated emulsion having the desired properties. An associative polymer is an amphihilic polymer, i.e., a polymer which comprises at least one fatty chain and hydrophilic units.

Accordingly, the present invention provides an aerated composition suitable for application to human skin, comprising:

an oily phase dispersed in an aqueous phase;

air or an inert gas;

at least one amphiphilic polymer; and at least one anionic surfactant, wherein the composition has a relative density ranging from 0.2 to 0.8.

The present invention also provides a method of treating, protecting, caring for, removing make-up from and/or cleansing the skin, lips and/or hair and/or for making up the skin and/or lips, comprising applying the inventive composition to the skin, lips and/or hair.

A subject-matter of the invention is consequently an aerated composition comprising, in a physiologically acceptable medium, an oily phase dispersed in an aqueous phase, characterized in that it contains air or inert gas in a sufficient amount to have a relative density ranging from 0.2 to 0.8 and in that it comprises at least one amphilic polymer and at least one anionic surfactant.

A more complete appreciation of the invention and many of the attendant advantages thereof will be readily obtained as the same becomes better understood by reference to the following detailed description.

DETAILED DESCRIPTION OF THE INVENTION

The composition of the invention exhibits a relative density which is lower than that of a conventional emulsion and yet nevertheless remains very stable over time (several months at room temperature). The aerated composition of the invention comprises air or inert gas bubbles and has a relative density ranging from 0.2 to 0.8 ($g/cm^3$) and preferably from 0.4 to 0.75, this relative density being measured at a temperature of approximately 25° C. and at atmospheric pressure. Inert gas may be nitrogen, helium or argon, or a mixture thereof. A mixture of air and any of these inert gases may also be used. The amount of air or inert gas necessary to obtain the wanted density is of at least 30% by volume, and it may range for example from 40 to 80% by volume, and preferably from 50 to 70% by volume with respect to the total volume of the composition.

The composition of the invention differs from foams obtained with a propellant (such as isobutane), such as shaving foams, by the fact that it stays as a stable foam over time, contrary to shaving foams which break down very quickly.

The composition of the invention advantageously comprises a physiologically acceptable medium, that is to say compatible with the skin, eyes and/or hair, and it can constitute in particular a cosmetic and/or dermatological composition.

This composition is an O/W (oil-in-water) emulsion which is neither greasy nor heavy and, as the external phase is the aqueous phase, it gives an impression of freshness on application to the skin.

The polymers which can be used in the present invention are amphiphilic polymers which comprise at least one fatty chain, therefore a hydrophobic part, and hydrophilic units, therefore a hydrophilic part. They are known as associative polymers because the percentage and/or the sizes of the hydrophobic groups are such that the said hydrophobic groups are capable of forming an association, in aqueous medium, with other hydrophobic groups.

The hydrophobic part can be in reduced number with respect to the remainder of the polymer chain, can be situated in the pendant position on the chain and can be distributed randomly (random copolymers) or distributed in the form of sequences or grafts (block copolymers or sequential copolymers).

The polymers which can be used in the composition of the invention can be soluble in water or dispersed in water to give microgels. These polymers are known as "swellable" in water. The polymers can be of any chemical nature; it is thus possible to choose optionally modified polymers of natural origin; radical polymers, in particular of vinyl or acrylic polymers; polycondensates; and their mixtures. These polymers can be ionic or nonionic and they are preferably anionic or nonionic.

Examples of optionally modified polymers of natural origin which can used in the composition of the invention include:

1) cellulose ethers possessing hydrophobic substituents, which substituents can be alkyl groups having a carbon number equal to or greater than 8. Examples of cellulose ethers of this type include, for example, hydroxyethylcellulose substituted by hydrophobic groups, such as the product sold under the name Natrosol Plus Grade 330 by Aqualon;
2) quaternized cationic celluloses modified by groups comprising at least one fatty chain, such as alkyl, arylalkyl or alkylaryl groups or their mixtures where the alkyl groups are preferably $C_8$–$C_{22}$ groups;
3) quaternized (cationic) alkylhydroxyethylcelluloses, such as the products sold under the names Quatrisoft LM 200, Quatrisoft LM-X 529-18-A, Quatrisoft LM-X 529-18-B ($C_{12}$ alkyl) and Quatrisoft LM-X 529-8 ($C_{18}$ alkyl) by Amerchol and the products sold under the names Crodacel QM, Crodacel QL ($C_{12}$ alkyl) and Crodacel QS ($C_{18}$ alkyl) by Croda;
4) galactomannans possessing hydrophobic substituents, in particular hydrophobic substituted guar gum. Some of these derivatives are disclosed in EP-A-281,360, incorporated herein by reference;
5) pullulans modified by hydrophobic groups, in particular cholesterol groups;
6) gelatins modified by hydrophobic groups, in particular modified by $C_6$ to $C_{18}$ alkyl groups;
7) mucopolysaccharides, such as those composed of glycosaminoglycan and of hyaluronic acid.

Examples of polycondensates which can be used in the context of the invention include: associative polyurethanes, which are nonionic sequential copolymers comprising, in the chain, both hydrophilic sequences of generally polyoxyethylene nature and hydrophobic sequences which can be aliphatic linking units alone or aliphatic linking units with cycloaliphatic and/or aromatic linking units. The resulting sequential copolymers can be of the triblock or multiblock type. The hydrophobic sequences can therefore be at each end of the chain (triblock copolymers comprising a central polyoxyethylene sequence) or distributed both at the ends of and in the chain (multisequential copolymers). They can also be as grafts or as a star.

Examples of associative polyurethanes include, for example, the polymers described in Zeying M. A., J. of Appl. Polymer Sci., vol. 49, 1509–27 (1993), incorporated herein by reference, and, among commercial polymers, of those sold under the names Rheolate 205, Rheolate 208 and Rheolate 204 by Rheox. These associative polyurethanes are sold in the pure form. It is also possible to use solutions or dispersions of these polymers, in particular in water or in aqueous/alcoholic medium. Mention may be made, as examples of such polymers, of the products sold under the names Serad FX1010 and Serad 1035 by Hüls or the products sold under the names Rheolate 255, Rheolate 278 and Rheolate 244 by Rheox. It is also possible to use the products sold under the names DW 1206F, DW 1206J, Acrysol RM 184, Acrysol 44 and Acrysol 46 by Röhm & Haas. It is also possible to use the product sold under the name DW 1206B by Röhm & Haas, comprising a $C_{20}$ alkyl chain and a urethane bond, sold at 20% on a dry basis in water.

Mention may be made, among the radical polymers which can be used in the composition according to the invention, of anionic acrylic polymers, in particular in aqueous dispersion, generally denoted under the name of HASE (hydrophobically modified alkali-soluble or swellable emulsion). These are acrylic copolymers which exist in the form of dispersions in water at acid pH and which can dissolve in water by complete neutralization of the anionic groups, that is to say beyond pH 8. Some of these dispersions can be partially crosslinked, which implies that complete neutralization does not bring about complete solubilization of the polymer particles but results in extensive swelling of these particles, also bringing about gelling of the medium.

These uncrosslinked or partially crosslinked copolymers are generally terpolymers obtained from (1) a monomer carrying a carboxylic acid group (acrylic or methacrylic acid), (2) a relatively water-insoluble monomer of the $C_1$ to $C_4$ acrylate or methacrylate type, such as ethyl acrylate, and (3) a third monomer carrying a hydrophobic group, which group can be attached in a pendant position on the main chain. This hydrophobic group can be a linear or branched alkyl chain comprising at least 8 carbon atoms, a cycloalkyl group, the alkyl radical of which comprises at least 8 carbon atoms, and/or an aryl group. The hydrophobic group can be attached to the main chain directly via an ether, ester, amide, carbamate or urea bond. It can also be attached to the main chain via a polyoxyethylene sequence, itself attached to the chain via an ether, ester, amide, carbamate or urea bond. In the latter case, the side groups are generally small grafts comprising a hydrophilic and hydrophobic sequence and the thickening properties with regard to aqueous media are better.

Such aqueous polymer dispersions are disclosed in particular in Shay, Surface Coatings International, 1993 (11), 446–453, and in the documents U.S. Pat. No. 4,421,902, U.S. Pat. No. 4,423,199, U.S. Pat. No. 4,663,385 and U.S. Pat. No. 4,384,096. Each of these publications is incorporated herein by reference. Mention may for example be made, as polymers of this type, of the products disclosed herein below and sold under the names Acusol 823, Acrysol 25 and Acusol 22 by Röhm & Haas.

Example of radical polymers which can be used in the composition of the invention include:

1) Copolymers of acrylic acid or of methacrylic acid with N-alkylacrylamides and in particular acrylic acid/N-alkylacrylamide copolymers in which the alkylacrylamides have a $C_1$ to $C_{20}$ alkyl group, such as those described in the article by Magny et al., Double Liaison [Double Bond], 451, p. 52–55 (1993), incorporated herein by reference. They can be obtained by direct copolymerization or by subsequent amidation of the acrylic acid chain. According to the procedures used, the hydrophobic alkyl groups can be distributed randomly (amidation in homogeneous organic solution) or in sequential form (amidation in aqueous medium, where the amine initially forms aggregates of micellar type).

2) Anionic radical copolymers, such as copolymers obtained from (a) a monomer comprising a carboxylic acid group, for example acrylic acid or methacrylic acid, and (b) at least one acrylate, methacrylate, ester or amide carrying hydrophobic cycloaliphatic or aromatic groups, such as isobornyl or adamantyl groups.

Mention may also be made of copolymers with perfluorinated monomers, in particular copolymers with perfluorohexyl (meth)acrylate; or copolymers between a monomer carrying a sulphonic acid group (in particular 2-acrylamido-2-methylpropanesulphonic acid or styrenesulphonic acid) and an alkyl(meth)acrylamide having at least 8 carbon atoms.

3) Nonionic acrylic copolymers and in particular copolymers of the acrylamide/N-alkylacrylamide type, such as those described in Goodwin et al., Polymer in Aqueous Media =Performance Through Association, [J. E. Glassed, Adv. Chem. Ser. 223; Am. Chem. Soc., Washington DC, p. 365 (1989)], incorporated herein by reference.

Mention may also be made of the following copolymers, used alone or alternatively as mixtures:

1) Copolymers of maleic anhydride and of monomers comprising at least one fatty chain, such as n-octadecyl vinyl ether/maleic anhydride copolymers, for example the product sold under the name Gantrez AN-8194 by ISP.

2) Copolymers of crotonic acid and of monomers comprising at least one fatty chain, such as vinyl acetate/crotonic acid/vinyl neodecanoate terpolymers, for example the product sold under the name Resine 28-2930 by National Starch; or vinyl acetate/crotonic acid/allyl stearate terpolymers, such as the products sold under the names Mexomere PV and PB by Chimex.

3) (Meth)acrylic acid polyme:rs modified by groups comprising at least one fatty chain or copolymers of (meth) acrylic acid and of monomers comprising at least one fatty chain, these monomers being chosen from hydrophobic monomers comprising a fatty chain or amphiphilic monomers comprising a hydrophobic part comprising a fatty chain and a hydrophilic part.

Mention may be made, by way of examples of copolymers of (meth)acrylic acid and of monomers comprising at least one fatty chain, of:

acrylic acid/$C_{10}$–$C_{30}$ alkyl acrylate crosslinked copolymers, such as the products sold under the names Pemulen TR1, Pemulen TR2, Carbopol 1382, Carbopol 1342 and Carbopol ETD 2020 by Goodrich;

(meth)acrylic acid/ethyl acrylate/alkyl acrylate copolymers, such as the product sold under the name Acusol 823 by Röhm & Haas and the product sold under the name Imperon R by Hoechst;

acrylic acid/vinyl isodecanoate crosslinked copolymers, such as the product sold under the name Stabylen 30 by 3V;

acrylic acid/vinylpyrrolidone/lauryl methacrylate terpolymers, such as the products sold under the names Acrylidone LM, ACP-1184 and ACP-1194 by ISP;

acrylic acid/lauryl (meth)acrylate copolymers, such as the products sold under the names Coatex SX by Coatex;

(meth)acrylic acid/alkyl acrylate/ polyethoxylated alkyl allyl ether terpolymers, such as the products sold under the names Rheovis-CR, -CR3, -CR2 and -CRX by Allied Colloids;

methacrylic acid/ethyl acrylate/ polyethoxylated stearyl allyl ether terpolymers, such as the products sold under the names Salcare-SC90 and -SC80 by Allied Colloids (polyethoxylated stearyl comprising 10 mol of ethylene oxide: CTFA name steareth-10);

methacrylic acid/ethyl acrylate/ polyoxyethylenated lauryl acrylate terpolymers, such as the product sold under the name Rheo 2000 by Coatex;

methacrylic acid/ethyl acrylate/ polyoxyethylenated stearyl methacrylate terpolymers, such as the products sold under the names Acrysol 22, Acrysol 25 and DW-1206A by Röhm & Haas;

methacrylic acid/ethyl acrylate/ polyoxyethylenated nonylphenol acrylate copolymers, such as the product sold under the name Rheo 3000 by Coatex;

acrylic acid/polyoxyethylenated stearyl monoitaconate copolymers or acrylic acid/ polyoxyethylenated cetyl monoitaconate copolymers, such as the products under the names 8069-72A and 8069-72B by National Starch;

methacrylic acid/butyl acrylate/hydrophobic monomer comprising a fatty chain copolymers, such as the product sold under the name 8069-146A by National Starch;

acrylic acid/$C_{15}$ alkyl acrylate/polyethylene glycol acrylate (28 mol of ethylene oxide) terpolymers, such as the product sold under the name Dapral GE 202 by Akzo;

salts of a partial fatty acid ester of an acrylic acid/ dimethylethanolamine polymer, such as the product sold under the name Dapral GE 202 DMA by Akzo;

acrylic acid/acrylate/amphiphilic monomer comprising a fatty chain comprising urethane groups copolymers, such as the product sold under the name Additol VXW 1312 by Hoechst;

acrylic polymers modified by hydrophobic groups comprising a fatty chain, such as the product sold under the name CS-0406 by Röhm & Haas.

The polymers used according to the invention can be used alone or as mixture. Furthermore, according to their nature, they can be used as such or in the form of aqueous solutions or of aqueous dispersions.

The composition according to the invention advantageously comprises an amount of polymer ranging from 0.05 to 15% by weight of active material, preferably from 0.1 to 8% and better still from 0.2 to 2% by weight of polymer active material with respect to the total weight of the composition.

The composition of the invention comprises at least one anionic surfactant. It is preferably a foaming anionic surfactant chosen from sulfates, ether sulfates and their salts. The choice is preferably made, among salts of sulfates and of ether sulfates, of the sodium and triethanolamine salts. Use may thus be made, as foaming anionic surfactant, of sodium lauryl ether sulfate and in particular those sold under the names Texapon by Henkel.

The composition of the invention generally comprises an amount of anionic surfactant ranging from 0.5 to 60% by weight, preferably from 1 to 30% by weight, better from 1 to 20% by weight and still better from 2 to 10% by weight with respect to the total weight of the composition.

The composition according to the invention can additionally comprise an emulsifier which can be chosen from any emulsifier conventionally used for O/W emulsions.

Mention may be made, as emulsifiers, of, for example:

(1) nonionic surfactants having an HLB of greater than or equal to 9, such as oxyethylenated esters of a fatty acid and of glycerol; oxyethylenated esters of a fatty acid and of sorbitan; oxyethylenated derivatives of a fatty acid; esters of a fatty acid and of a sugar and in particular sucrose fatty esters, such as sucrose stearate, for example the product sold under the name Tegosoft PSE 141G by Goldschmidt; alkyl polyglucoside ethers; and their mixtures;

(2) silicone emulsifiers, such as oxyethylenated polydimethylmethylsiloxanes (dimethicone copolyol), such as, for example, that sold under the name "DC2-5695" by Dow Corning.

The composition according to the invention can comprise, for example, from 0.5 to 30%, preferably from 2 to 15% and better still from 4 to 10% by weight of emulsifier(s) with respect to the total weight of the composition.

The nature of the oily phase of the emulsion according to the invention is not critical. The oily phase can thus be composed of any fatty substance, in particular oils, conventionally used in the cosmetic and dermatological fields. The oily phase contains at least one oil, preferably at least 1% by weight of at least one oil and better at least 2% by weight of at least one oil, with respect to the total weight of the composition.

Mention may be made, among oils which can be used in the composition of the invention, of, for example, vegetable oils, such as apricot oil, mineral oils, such as liquid petrolatum, synthetic oils, such as isohexadecane; volatile or non-volatile silicon oils; and fluorinated oils. Mention may in particular be made, as volatile silicone oils, of cyclic polydimethylsiloxanes or cyclomethicones which comprise from approximately 3 to 9 silicon atoms and preferably from 4 to 6 silicon atoms, such as cyclohexadimethylsiloxane or cyclohexamethicone and cyclopentadimethylsiloxane or cyclopentamethicone. The other fatty substances capable of being present in the oily phase can be, for example, fatty acids, fatty alcohols, such as cetyl alcohol, and waxes.

The composition according to the invention advantageously comprises from 1 to 40% by weight, preferably from 2 to 30% and better still from 5 to 20% by weight of oily phase with respect to the total weight of the composition.

The aqueous phase of the emulsion constituting the composition of the invention can represent from 15 to 97.95% by weight, preferably from 57 to 93% and better still from 75 to 90% by weight with respect to the total weight of the composition.

As will be readily appreciated by those skilled in the art, the composition of the invention can also comprise adjuvants usual in the cosmetics field, such as active principles, humectants, preservatives, antioxidants, complexing agents, solvents, fragrances, screening agents, bactericides, odour absorbers, colouring materials (pigments or soluble dyes) and lipid vesicles. The amounts of these various adjuvants are those conventionally used in the field under consideration, for example from 0.01 to 20% of the total weight of the composition. These adjuvants, according to their nature, can be introduced into the fatty phase, into the aqueous and/or into the lipid vesicles.

The present invention also relates to the process for the manufacture of the composition according to the invention. This process consists in preparing the emulsion in a conventional way by introducing the oily phase into the aqueous phase with stirring, for example in a device of Moritz type, and in then introducing air into the emulsion obtained with stirring ranging from 500 to 2000 revolutions/minute, at a temperature ranging from 20° C. to 80° C. and preferably from 40° C. to 60° C., under an air inlet pressure ranging from to 8 bar ($2.10^5$ to $8.10^5$ Pa) and preferably from 3 to 6 bar ($3.10^5$ to $6.10^5$ Pa).

Another aspect of the present invention is therefore a process for the manufacture of an aerated composition based on an oil-in-water emulsion which consists:

(1) in preparing an oil-in-water emulsion containing at least one amphiphilic polymer and at least one anionic surfactant, in a conventional way by dispersing the oily phase in the aqueous phase, (2) in introducing air into the emulsion obtained with stirring ranging from 500 to 2000 revolutions/minute, at a temperature ranging from 20° C. to 80° C. and under an air inlet pressure ranging from 2 to 8 bar.

According to a preferred embodiment of the invention, the introduction of the air into the emulsion is carried out in an expansion device comprising a mixing head comprising a rotor and a stator, such as, for example, the "Minimondo-type Mondomixer" supplied by Mondomix. The emulsion is transported via a pump into the expansion head, where the emulsion and the air are simultaneously injected and homogeneously mixed by virtue of the cutting action of the lugs of the rotor and stator of the device, which ensure even distribution of the air in the product. The speed of the rotor of the device, the temperature of the vessel and pipes, and the inlet pressure of the air into the mixing head and the air flow rate are appropriately regulated. The pressure of the mixing head is regulated by a pressure regulator. The flow rate of the emulsion at the outlet of the device depends on the rate of the pump at the vessel outlet.

Preferably, in the expansion device, the stirring speed during the introduction of the air is 1000 revolutions/minute, the temperature is 50° C. and the air inlet pressure is 4 bar.

The air bubbles in the aerated emulsion obtained according to the process of the invention advantageously have a size ranging from 20 $\mu$m to 500 $\mu$m and preferably ranging from 100 $\mu$m to 300 $\mu$m.

The composition according to the invention is applied in a large number of treatments, in particular cosmetic treatments, of the skin, the lips and hair, including the scalp, in particular for treating, protecting, caring for, removing make-up from and/or cleansing the skin, lips and/or hair and/of for making up the skin and/or lips. It can also be intended for treating dry skin and/or dry lips.

The composition according to the invention can be used, for example, as care, make-up removal and/or cleansing product for the face, in the form of creams or of milks, or as make-up products (skin and lips), for example foundations, by incorporation of dyes.

A further aspect of the invention is consequently the cosmetic use of the composition as defined above for treating, protecting, caring for, removing make-up from and/or cleansing the skin, lips and/or hair and/or for making up the skin and/or lips.

Another aspect of the invention is a process for the cosmetic treatment of the skin, including the scalp, hair and/or lips, characterized in that a composition as defined above is applied to the skin, hair and/or lips.

Another aspect of the invention is the use of the composition as defined above in the manufacture of a composition intended for caring for dry skin and/or dry lips.

EXAMPLES

Having generally described this invention, a further understanding can be obtained by reference to certain specific examples which are provided herein for purposes of illustration only and are not intended to be limiting unless otherwise specified. The amounts are given therein as % by weight, unless specified otherwise.

Example

| Care Cream | |
|---|---|
| Oily phase: | |
| Apricot oil | 10% |
| Sodium lauryl ether sulfate | 2% |
| Cetyl alcohol | 2% |
| Sucrose stearate (Tegosoft PSE 141G) | 5% |
| Aqueous phase: | |
| Pemulen TR2 | 0.4% |
| Preservatives | 1% |
| Water | q.s. to 100% |

Procedure:

The emulsion is prepared conventionally in a Moritz device. It is then placed in the pump of the Minimondo-type expansion device. It is transported from the pump to the expansion head, into which it is injected with air and homogeneously mixed with the air. The flow rate of the emulsion is 30 kg/hour, the speed of the rotor is 1000 revolutions/minute, the temperature of the vessel and pipes is 50° C. and the inlet pressure is 4 bar.

A cream with a very light texture which has the appearance of a fine foam is obtained, which cream can be used as a day cream.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-04968, filed on Apr. 20, 1999, and incorporated herein by reference in its entirety.

What is claimed is:

1. An aerated composition suitable for application to human skin, comprising:
   an oily phase dispersed in an aqueous phase;
   at least 30% by volume of air or an inert gas with respect to the total volume of the composition;
   at least one amphiphilic polymer; and
   at least one anionic surfactant,
   wherein the composition has a relative density ranging from 0.2 to 0.8.

2. The composition of claim 1, which has a relative density ranging from 0.4 to 0.75.

3. The composition of claim 1, wherein the amount of air or inert gas ranges from 40 to 80% by volume with respect to the total volume of the composition.

4. The composition of claim 1, wherein the amphiphilic polymer is selected from the group consisting of optionally modified polymers of natural origin, radical polymers, polycondensates and mixtures thereof.

5. The composition of claim 1, wherein the amphiphilic polymer is a polymer of natural origin selected from the group consisting of cellulose ethers possessing hydrophobic substituents, quaternized cationic celluloses modified by groups comprising at least one fatty chain, quaternized alkylhydroxyethylcelluloses, galactomannans possessing hydrophobic substituents, pullulans modified by hydrophobic groups, gelatins modified by hydrophobic groups, and mucopolysaccharides.

6. The composition of claim 1, wherein the amphiphilic polymer is selected from the group consisting of associative polyurethanes.

7. The composition of claim 1, wherein the amphiphilic polymer is a radical polymer selected from the group consisting of copolymers of acrylic acid or of methacrylic acid with N-alkylacrylamides, copolymers obtained from a monomer comprising a carboxylic acid group and from an acrylate, methacrylate, ester or amide carrying hydrophobic cycloaliphatic or aromatic groups, nonionic acrylic copolymers, copolymers of maleic anhydride and of monomers comprising at least one fatty chain, copolymers of crotonic acid and of monomers comprising at least one fatty chain, (meth)acrylic acid polymers modified by groups comprising at least one fatty chain, and copolymers of (meth)acrylic acid and of monomers comprising at least one fatty chain.

8. The composition of claim 1, wherein amphiphilic polymer is selected from the group consisting of acrylic acid/$C_{10}$–$C_{30}$ alkyl acrylate crosslinked copolymers, (meth) acrylic acid/ethyl acrylate/alkyl acrylate copolymers, acrylic acid/vinyl isodecanoate crosslinked copolymers, acrylic acid/vinylpyrrolidone/lauryl methacrylate terpolymers, acrylic acid/lauryl (meth)acrylate copolymers, (meth)acrylic acid/alkyl acrylate/polyethoxylated alkyl allyl ether terpolymers, methacrylic acid/ethyl acrylate/ polyethoxylated stearyl allyl ether terpolymers, methacrylic acid/ethyl acrylate/polyoxyethylenated lauryl acrylate terpolymers, methacrylic acid/ethyl acrylate/ polyoxyethylenated stearyl methacrylate terpolymers, methacrylic acid/ethyl acrylate/polyoxyethylenated nonylphenol acrylate copolymers, acrylic acid/polyoxyethylenated stearyl monoitaconate copolymers or acrylic acid/ polyoxyethylenated cetyl monoitaconate copolymers, acrylic acid/$C_{15}$ alkyl acrylate/polyethylene glycol acrylate (28 mol of ethylene oxide) terpolymers, acrylic acid/ acrylate/amphiphilic monomer comprising a fatty chain comprising urethane groups copolymers, acrylic polymers modified by hydrophobic groups comprising a fatty chain, and mixtures thereof.

9. The composition of claim 1, comprising an amount of amphiphilic polymer(s) ranging from 0.05 to 15% by weight of active material with respect to the total weight of the composition.

10. The composition of claim 1, wherein the anionic surfactant is selected from the group consisting of sulfates, ether sulfates, and salts thereof.

11. The composition of claim 1, wherein the anionic surfactant is sodium lauryl ether sulfate.

12. The composition of claim 1, comprising an amount of anionic surfactant(s) ranging from 1 to 20% by weight with respect to the total weight of the composition.

13. The composition of claim 1, further comprising at least one emulsifier.

14. The composition of claim 1, further comprising an amount of emulsifier(s) ranging from 0.5 to 30% by weight with respect to the total weight of the composition.

15. The composition of claim 1, wherein the oily phase represents from 1 to 40% by weight with respect to the total weight of the composition.

16. A method of treating, protecting, caring for, removing make-up from and/or cleansing the skin, lips and/or hair and/or for making up the skin and/or lips, comprising applying the composition of claim 1 to the skin, lips and/or hair.

17. A process for the manufacture of an aerated composition based on an oil-in-water emulsion, comprising:
   (1) dispersing an oily phase in an aqueous phase in the presence of at least one amphiphilic polymer and at least one anionic surfactant, to produce an oil-in-water emulsion, (2) introducing air into the emulsion from (1) with stirring ranging from 500 to 2000 revolutions/minute, at a temperature ranging from 20° C. to 80° C. and under an air inlet pressure ranging from 2 to 8 bar;

wherein said introduction is carried out in an expansion device.

* * * * *